(12) United States Patent
Seip et al.

(10) Patent No.: US 11,141,179 B2
(45) Date of Patent: Oct. 12, 2021

(54) SETTING OF SONOTHROMBOLYSIS ULTRASOUND OUTPUT POWER

(71) Applicant: KONINKLIJKE PHILIPS N.V., Eindhoven (NL)

(72) Inventors: Ralf Seip, Carmel, NY (US); Sonia Souza, Bothell, WA (US); Jeffry Earl Powers, Bainbridge Island, WA (US); William Tao Shi, Wakefield, MA (US); Terrence James Sweeney, Redmond, WA (US); Sarah Rhoades Baxter, Hansville, WA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 363 days.

(21) Appl. No.: 15/534,549

(22) PCT Filed: Nov. 23, 2015

(86) PCT No.: PCT/IB2015/059026
§ 371 (c)(1),
(2) Date: Jun. 9, 2017

(87) PCT Pub. No.: WO2016/092396
PCT Pub. Date: Jun. 16, 2016

(65) Prior Publication Data
US 2019/0000493 A1 Jan. 3, 2019

Related U.S. Application Data
(60) Provisional application No. 62/090,719, filed on Dec. 11, 2014.

(51) Int. Cl.
*A61B 17/225* (2006.01)
*A61B 8/08* (2006.01)
(Continued)

(52) U.S. Cl.
CPC ........ *A61B 17/2256* (2013.01); *A61B 8/0808* (2013.01); *A61B 8/0858* (2013.01);
(Continued)

(58) Field of Classification Search
CPC ........... A61N 7/00; A61N 7/22; A61N 7/225; A61N 2007/0004; A61N 2007/0039;
(Continued)

(56) References Cited

U.S. PATENT DOCUMENTS

2006/0240381 A1* 10/2006 Rizoiu ................... A61C 17/02
433/80
2008/0082026 A1* 4/2008 Schmidt ................... A61N 7/02
601/2

(Continued)

FOREIGN PATENT DOCUMENTS

WO 2012042434 A1 4/2012
WO WO-2012042494 A1 * 4/2012 ............... A61B 8/06
(Continued)

OTHER PUBLICATIONS

Barlinn K., et al., "Exploratory analysis of estimated acoustic peak rarefaction pressure, recanalization, and outcome in the transcranial ultrasound in clinical sonothrombolysis trial", Journal of Clinical Ultrasound, Jul./Aug. 2013; vol. 41, Issue 6; pp. 354-360 (Abstract).

*Primary Examiner* — Katherine L Fernandez

(57) ABSTRACT

An apparatus for patient-specific adjusting of ultrasound output pressure includes a controller (118) configured for adjusting, based on an estimate of thickness of a temporal bone (140) in a head of a medical treatment recipient, a pressure setting. It may also be based on treatment depth (134). Ultrasound at the adjusted pressure setting is applied. A user interface may be provided for user entry of the estimate, the user interface being further configured for user indication of the treatment depth. Both the entered estimate and the indicated treatment depth may be used in calculating (Continued)

ultrasound attenuation (148). The user indication can be interactive by virtue of designating, on a display, a location of a treatment target. The calculated attenuation may be a value, in decibels, that is in a range from 0.9×(2.70×0.1+16.60×T+0.87×(D−T−0.1)+3.02) to 1.1×(2.70×0.1+16.60×T+0.87×(D−T−0.1)+3.02), where T is the estimate in centimeters and D is the treatment depth in centimeters.

13 Claims, 2 Drawing Sheets

(51) Int. Cl.
| | | |
|---|---|---|
| A61N 7/00 | (2006.01) | |
| A61B 17/22 | (2006.01) | |
| A61B 34/00 | (2016.01) | |
| A61B 90/00 | (2016.01) | |
| A61B 17/00 | (2006.01) | |

(52) U.S. Cl.
CPC .......... *A61B 8/0875* (2013.01); *A61B 8/5223* (2013.01); *A61B 17/22004* (2013.01); *A61B 34/25* (2016.02); *A61N 7/00* (2013.01); *A61B 2017/00106* (2013.01); *A61B 2090/378* (2016.02); *A61N 2007/0004* (2013.01); *A61N 2007/0039* (2013.01); *A61N 2007/0052* (2013.01)

(58) Field of Classification Search
CPC ..... A61B 8/481; A61B 8/5523; A61B 8/0808; A61B 8/0858; A61B 8/0875; A61B 17/2256
See application file for complete search history.

(56) References Cited

U.S. PATENT DOCUMENTS

| | | | |
|---|---|---|---|
| 2010/0210940 A1 | 8/2010 | Bradley et al. | |
| 2012/0083717 A1 | 4/2012 | Alleman et al. | |
| 2012/0083718 A1* | 4/2012 | Alleman | A61N 7/00 601/2 |
| 2012/0095305 A1* | 4/2012 | Wang | A61B 5/0075 600/323 |
| 2012/0165670 A1* | 6/2012 | Shi | G01S 7/52049 600/442 |
| 2013/0131495 A1* | 5/2013 | Konofagou | A61B 8/0808 600/411 |
| 2013/0172906 A1* | 7/2013 | Olson | A61B 34/74 606/130 |
| 2014/0275947 A1* | 9/2014 | Fonte | A61B 6/5217 600/407 |
| 2015/0272601 A1* | 10/2015 | Dixon | A61B 17/2202 604/22 |
| 2016/0279449 A1 | 9/2016 | Powers et al. | |
| 2018/0001114 A1* | 1/2018 | Li | A61N 7/00 |

FOREIGN PATENT DOCUMENTS

| | | |
|---|---|---|
| WO | 2014207665 A2 | 12/2014 |
| WO | 2015075603 A1 | 5/2015 |
| WO | 2016092414 A1 | 6/2016 |

\* cited by examiner

SETTING OF SONOTHROMOBOLYSIS ULTRASOUND OUTPUT POWER

This application is the U.S. National Phase application under 35 U.S.C. § 371 of International Application No. PCT/M2015/059026, filed on Nov. 23, 2015, which claims the benefit of U.S. Provisional Application Ser. No. 62/090,719, filed Dec. 11, 2014. These applications are hereby incorporated by reference herein.

FIELD OF THE INVENTION

The present invention relates to setting an output power for emitting ultrasound intracranially through the temporal bone and, more particularly, to performing the setting based on a priori information.

BACKGROUND OF THE INVENTION

Sonothrombolysis (STL) treatments for acute stroke rely on ultrasound energy (targeting the clot) delivered through the temporal bone and microbubbles injected systemically to achieve clot dissolution and vessel recanalization.

Sonothrombolysis treatments are being investigated by a multitude of researchers and clinicians for their potential role in treating acute stroke. In STL treatments, ultrasound pulses are delivered through the skull temporal bone, targeted at the clot that causes the occlusion. Microbubbles, an ultrasound contrast agent, are introduced into the bloodstream, as their mechanical oscillation at the clot site due to the applied ultrasound energy has been shown to over time dissolve the clot and achieve vessel recanalization for acute stroke treatment. One of the advantages of STL treatments is that they can be performed without the use of drugs (such as t-PA, or tissue plasminogen activator, a common "clot-busting" drug), which carry with them significant restrictions to their use, and overall low treatment success.

One challenge associated with STL treatments is that the ultrasound energy is delivered to the clot location inside the patient's brain through the skull. Several acoustic windows are available in the skull that allow ultrasound energy to be transmitted into the brain. For STL, the best acoustic window is the temporal bone, located at the sides of the skull, as most strokes occur due to the occlusion of the middle cerebral arteries, which are located behind the temporal bone, and can be visualized with diagnostic ultrasound and color Doppler. Even so, the temporal bone attenuates ultrasound significantly, degrading the ability to image the brain, and also making it more difficult to deliver the required ultrasound energies for successful STL treatments.

Another challenge associated with STL treatments is that the thickness and consequent attenuation of the temporal bone vary from patient to patient, potentially resulting in either higher or lower ultrasound energies being delivered to the clot location, with the potential of causing undesired bioeffects (in the case of a thinner temporal bone yielding higher ultrasound energies and pressure amplitudes in the brain), or not being able to dissolve the clot at all (in the case of a thicker temporal bone yielding lower ultrasound energies and pressure amplitudes in the brain).

A number of dose determination approaches have met with difficulty in controlling microbubble concentration at the occlusion site, difficulty in measuring harmonic content and in situ pressure (ISP) accurately, the need for specialized equipment and extra facilities, etc.

For STL treatments, ultrasound pulses travel from the transducer/array (which is mounted on and held in place by the headset against a patient's temporal bone) through multiple layers including skin, skull, brain tissue, etc. Ultrasound energy is not only attenuated within each of the multiple layers but also reflected from interfaces between neighboring layers. The transcranial attenuation considered here is the total attenuation from the skin surface to the stroke occlusion site. This attenuation affects the effective ultrasound pressure amplitude at the site of the occlusion, and is an important parameter in the safety and efficacy of the sonothrombolysis therapy.

TUCSON trial investigators recently estimated the in vivo acoustic pressure amplitude at the arterial occlusion site for each subject of the TUCSON trial with computed tomography (CT) scans eligible for measurements. See Barlinn K, Tsivgoulis G, Molina C A, Alexandrov D A, Schafer M E, Alleman J, Alexandrov A V; TUCSON Investigators, "Exploratory analysis of estimated acoustic peak rarefaction pressure, recanalization, and outcome in the transcranial ultrasound in clinical sonothrombolysis trial." J Clin Ultrasound. 2013; 41(6):354-60. The TUCSON trial (NCT00504842) was a phase II randomized clinical trial of systemic tPA therapy versus systemic tPA therapy with 2 hours of 2 megahertz (MHz) transcranial Doppler (TCD) exposure and escalating doses of perflutren-lipid microspheres, initiated within 3 hours from symptom onset. The CT measurements were available for a total of 20 stroke patients with a mean occlusion depth of 5.08±0.766 cm (mean and standard deviation, respectively) from the skin surface. All of the patients had adequate acoustic windows on the temporal bone for ultrasound transmission at 2 MHz.

SUMMARY OF THE INVENTION

The quality of the temporal acoustic windows in stroke patients has been extensively studied using either 1.6-2.0 MHz TCD or transcranial ultrasound imaging.

The present inventors have discovered that, in using a lower frequency for STL, i.e., 1.0 MHz versus 1.6 MHz or higher, the effectiveness is equivalent or better and the variance in total attenuation, due for example to layer thickness and particularly that of the temporal bone, significantly drops. More specifically, the largest in situ pressure (ISP) variation due to brain attenuation and temporal bone attenuation at a fixed treatment depth of 5 centimeters (cm) can be limited within a factor of 2, when patients with the thinnest temporal bone are compared to those with the thickest temporal bone.

This can be coupled with the observation that in situ pressures of approximately 200-400 kilopascals (kPa) at 1 MHz are needed for effective clot lysis without detrimental bioeffects and that in situ pressures of 600-800 kPa sometimes result in detrimental bioeffects.

Although this suggests having at least some power/pressure control of the ultrasound dose, it is possible to fine-tune (or have more control over) dose determination, especially from the perspective of the clinician and console operator.

In one aspect of what is proposed herein, an apparatus for patient-specific adjusting of ultrasound output pressure includes a controller configured for adjusting, based on an estimate of thickness of a temporal bone in a head of a medical treatment recipient, a pressure setting. It also includes an ultrasound-emitting device for applying ultrasound at the adjusted pressure setting. The adjusting may also be based on a treatment depth.

Details of the novel technology for intracranial sonothrombolysis ultrasound-dose pre-quantification are set forth further below, with the aid of the following drawings, which are not drawn to scale.

DETAILED DESCRIPTION OF EMBODIMENTS

Figure 1:
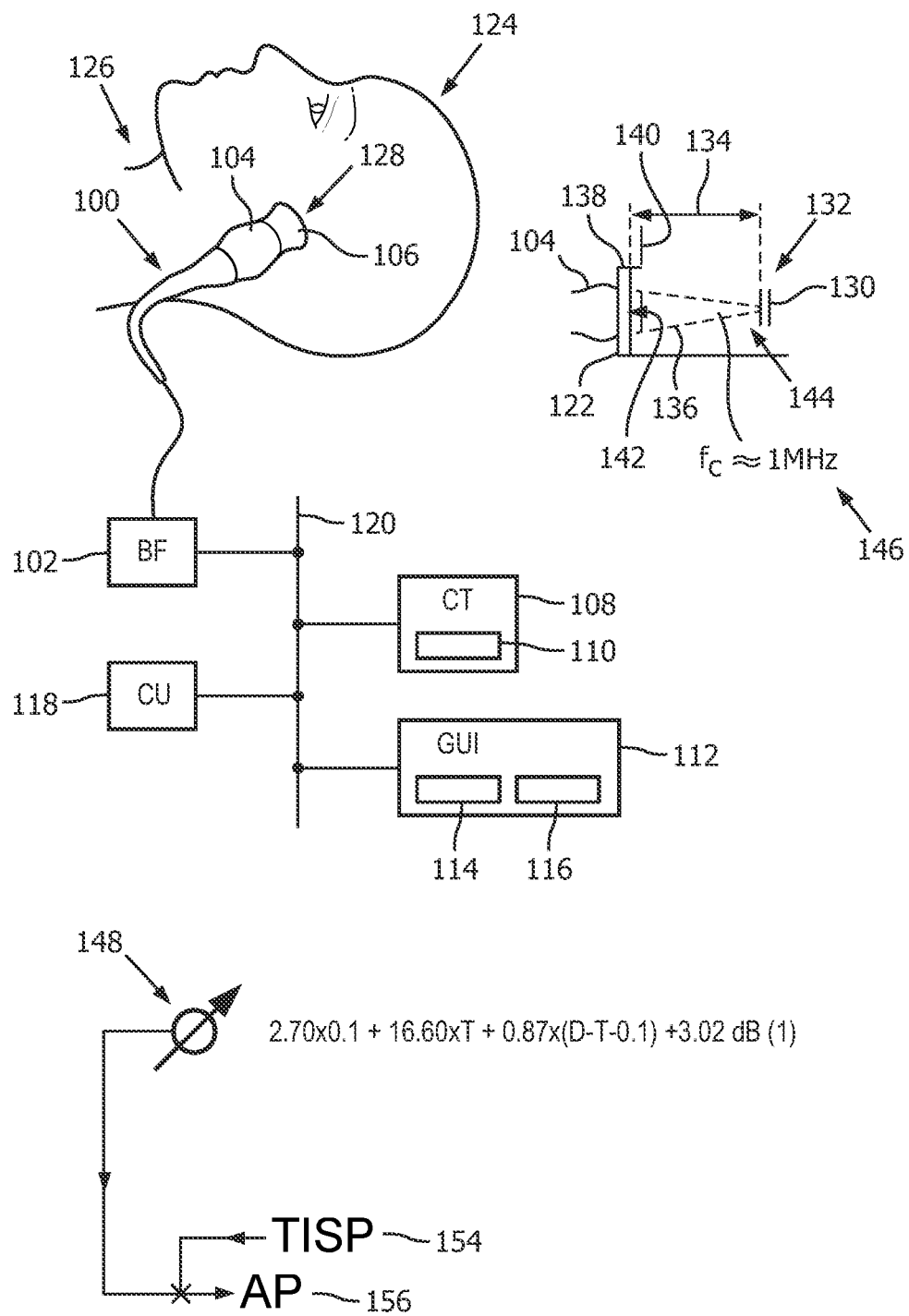
FIG. 1 is a schematic and conceptual diagram exemplary of a patient-specific technology for pre-adjusting ultrasound output power to be applied intracranially through the temporal bone window.

An apparatus 100, depicted in FIG. 1 by way illustrative and non-limitative example, for effecting patient-specific technology for pre-adjusting ultrasound output power to be applied intracranially through the temporal bone window includes a transmit and receive beamformer 102 and, communicatively connected to the beamformer, an ultrasound imaging probe 104. The probe 104 incorporates an ultrasound transducer 106. The apparatus 100 is configured for emitting ultrasound for sonothrombolysis via the transducer 106. Microbubbles suspended in a liquid may be injected by a syringe or pumped intravenously via a catheter, these instruments not being shown in FIG. 1. The transducer 106 may be configured also for ultrasound imaging. Alternatively, a second transducer (not shown) can be arranged, e.g., concentrically within the probe 104 for this purpose. As a further alternative, an imaging-capable transducer may reside in a second probe (not shown).

Also included in the apparatus 100 optionally is a computed tomography (CT) scanner 108 which may have an automatic image segmentation tool 110, a version of which may also be available for the ultrasound modality.

The apparatus 100 includes a graphic user interface (GUI) 112 which includes a display 114 and user controls 116.

The apparatus 100 further includes a controller 118, it along with the beamformer 102, CT scanner 108 and GUI 112 being mutually communicatively connected as by a data communication and power bus 120. The controller 118 direct various functions such as ultrasound pressure setting adjusting and the preparatory step of applying imaging tools such as automatic segmentation to derive temporal bone thickness.

The transducer 106 has an ultrasound-interface surface, or "face", 122 that is applicable to the head 124 of a human or animal patient 126. More particularly, it is applied for therapy to the ipsalateral temple area 128, an area of the temple closest to clot 130. The clot 130 is shown occluding circulation within a blood vessel 132. Within a treatment depth 134 from the face 122 to the center of the clot-induced occlusion region 130, a therapeutic ultrasound beam 136 passes first through a skin layer 138, then through a temporal bone 140 which is part of the skull and has a respective thickness 142, and then through brain tissue 144 until reaching the clot.

Determining which temple is the ipsalateral one involves first diagnosing a stroke and locating it within the brain. The ultrasound imaging and/or CT of the apparatus 100 can be used for this, although this information may be obtained prior to using the apparatus proposed herein.

Also, due to anatomical variability, some, perhaps about 20%, of patients have acoustic temporal windows that are inadequate for sonothrombolysis. The screening out of such patients from the instant treatment may be done via the ultrasound imaging of the apparatus 100, or via ultrasound or another imaging modality prior to use of what is proposed herein.

The therapeutic ultrasound beam 136 has a central frequency 146 at approximately 1 MHz, and which is in a range from 0.8 to 1.2 MHz or, in some cases, from 0.9 to 1.1 MHz.

An ultrasound beam, for therapy or imaging, travels through 3 layers of acoustically lossy media: the skin layer 138 (0.1 cm thick), the temporal bone 140, and brain tissue 144. The attenuation within each of the 3 layers 138, 140, 144 is assumed to be proportional to the thickness of the layer.

The total attenuation ($A_{total}$) includes skin attenuation ($A_{skin}$), temporal bone attenuation ($A_{bone}$), brain tissue attenuation ($A_{brain}$), as well as transmission loss (TL) due to the skin-to-skull and skull-to-brain reflection, i.e., $A_{total} = A_{skin} + A_{bone} + A_{brain} + TL$. The attenuation coefficients for skin, temporal bone and brain tissue at 1 MHz are 2.70 dB/cm, 16.60 dB/cm and 0.87 dB/cm, respectively. The transmission loss (TL) is 3.02 dB. Using these parameters, transcranial attenuation 148 at 1 MHz can be calculated from the following equation (attenuation in dB and distance in cm) shown in FIG. 1 for the typical case of a skin thickness of 0.1 cm:

$$A_{total}(D) = 2.70 \times 0.1 + 16.60 \times T + 0.87 \times (D - T - 0.1) + 3.02 \quad (1)$$

where T is the thickness (in cm) 142 of the temporal window and D is the depth (in cm) 134 of the treatment target point 130. Attenuation values for the various tissue layers in equation (1) are average values for these structures obtained from the literature, and highlighted in the table below.

The average temporal bone thickness 142 is 0.30 cm with a standard deviation of 0.08 cm; although, the smallest reported temporal bone thickness found by the instant inventors is 0.07 cm. As seen from equation (1), this range of thickness 142 represents a significant part of the total variation in attenuation 148; although, the present inventors have discovered that, at 1 MHz, the thickness 142 of the temporal bone 140 is, unlike at higher frequencies, not the dominant factor in the overall transcranial ultrasound attenuation path. This is seen from the table below of typical transcranial attenuation for stroke patients with average and minimal temporal bone thickness 142:

| Transcranial Attenuation for the mean depth of 5.08 cm | | Attenuation within each layer | | | Transmission Loss | Total Attenuation |
|---|---|---|---|---|---|---|
| | | skin | bone | brain | | |
| Average | attenuation coefficient (dB/cm) | 2.70 | 16.60 | 0.87 | 3.02 | 12.3 |
| | layer thickness (cm) | 0.10 | 0.30 | 4.68 | | |
| | attenuation (dB) | 0.27 | 4.98 | 4.07 | | |
| Minimal | attenuation coefficient (dB/cm) | 2.70 | 16.60 | 0.87 | 3.02 | 8.7 |
| | layer thickness (cm) | 0.10 | 0.07 | 4.91 | | |
| | attenuation (dB) | 0.27 | 1.16 | 4.27 | | |

In particular, the attenuation of the temporal bone (excluding transmission loss) on average accounts for only 4.98 dB at 1 MHz, i.e., 40% of the total attenuation of 12.3 dB at 5.08 cm.

The difference between average and minimal transcranial attenuation, shown in the table above to be 12.3−8.7=3.6 dB at the treatment depth 134 of 5.08 cm is an estimate that holds for any treatment depth. The consequent variation of in situ pressure (ISP) at the treatment site 130, for a given pressure at the transducer face 122, is 10(3.6/20)=1.51. Thus, the ISP delivered from across the thinnest temporal bone 140** is 51% higher than that for the temporal bone of average thickness. The increase over a whole range from virtually the thickest to virtually the thinnest entails an increase within 100%.

This corresponds to an in situ ultrasound pressure variation by merely a factor of 2, and a resulting ultrasound intensity/power/energy variation by merely a factor of 4.

Figure 2:
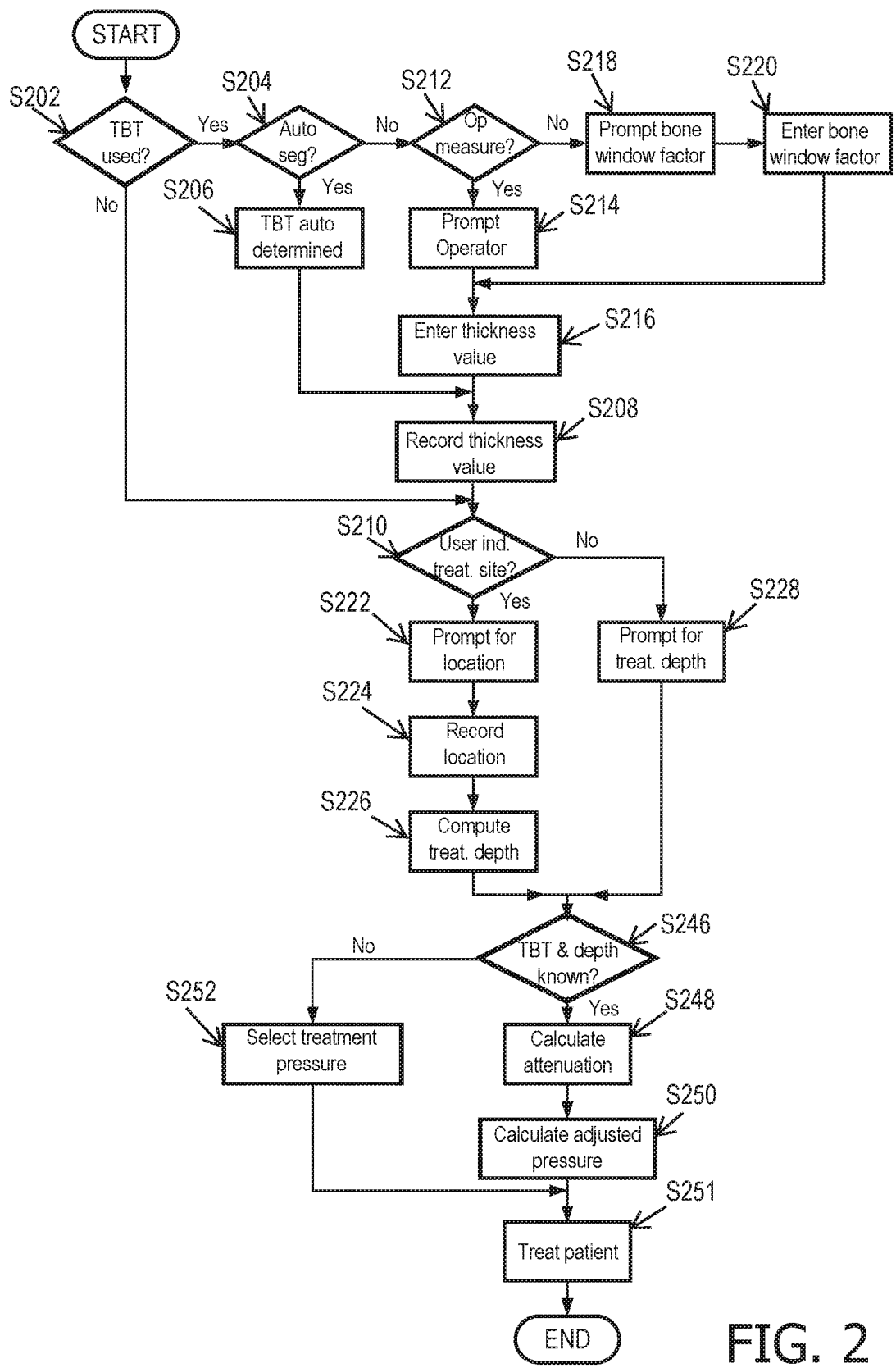
FIG. 2 is a particular variation on methodology performed according to FIG. 1.

FIG. 2 provides an example of a procedure for carrying out what is proposed herein.

If the temporal bone thickness 142 of the medical treatment recipient 126 is to be used, or determined and used (step S202), query is made as to whether automatic segmentation of the temporal bone is to be performed (step S204). The automatic segmentation is performed by segmentation tool 110 of the CT scanner 108, or by a segmentation tool of an ultrasound scanner of the apparatus 100. If automatic segmentation is performed (step S204) the thickness 142 is automatically determined (step S206). The thickness is recorded (step S208) and query is made as to whether there is to be a user indication of the treatment site (step S210).

Referring back to step S204, if on the other hand, the automatic segmentation is not to be performed (step S204), query is made as to whether the operator will measure, or obtain a measurement of, the thickness 142 (step S212). If the operator will measure, or obtain a measurement of, the thickness 142 (step S212), an on-screen prompt issues for the operator to do so (step S214). The operator then enters the thickness value (step S216). If, on the other hand, the operator will not measure, nor obtain a measurement of, the thickness 142 (step S212), an on-screen prompt issues for the operator to enter a qualitative temporal bone window factor (step S218. The operator will then, from an ultrasound image taken from the acoustic temporal window, assess how easy it is to identify features of the brain, and accordingly enter a qualitative temporal bone window factor (step S220). The controller 118 will then use this factor to estimate the temporal bone thickness 142. Processing then branches forward to the value entry step S216.

If there will be a user indication of the treatment site 130 (step S210), the user is prompted onscreen for designating the location of the treatment site 130 (step S222). The designated location is recorded (step S224). From the designated location, the treatment depth 134 is computed (step S226). Otherwise, if there will not be a user indication of the treatment site (step S210), the user is prompted onscreen for the treatment depth 134 (step S228). The treatment depth 134 may be extracted using the CT scanner 108. The extraction can be accomplished, as by CT angiography, manually via the clinician or automatically from the X-ray image using image processing. So, the CT scanner 108 can be the source both the temporal bone thickness 142 reading and the treatment depth 134 reading.

In either case (step S210), query is made as to whether the treatment depth 134 and temporal bone thickness 142 are accurately known (step S246). If they are accurately known (step S246), equation (1) is utilized to calculate the attenuation 148 (step S248). The attenuation 148 is multiplied by the targeted in situ pressure (TISP) 154 to yield an adjusted pressure 156 (step S250). The adjusted pressure 153 is applied in treating the patient 126 (step S251). Otherwise, if the treatment depth 134 and temporal bone thickness 142 are only approximately known (step S246), a treatment pressure is selected from a number of possible selections which could be, for example, three or more, e.g., a low pressure, a middle pressure, and a high pressure. For instance, if the qualitative temporal bone window factor is used, the temporal bone width estimate is approximate, but may indicate a thick temporal bone. Thus, a high pressure is selected, that pressure being predefined. If there were simply a single pressure, i.e., no choice as to pressure, that single pressure, no matter how low or high, would be inadequate to at once provide for safety no matter how thin the temporal bone is while providing for sufficient lysis no matter how thick the patient's temporal bone is. However, as discovered by the instant inventors and as discussed herein above, at 1 MHz, lysis is effective and the variation of pressure to be applied from the thinnest to the thickest temporal bone is limited to factor of 2. Accordingly, the bit of extra information provided by selecting from among low, middle and high pressure results in safe and effective sonothrombolysis at 1 MHz for the patient being treated. On the one hand, the best estimate of temporal bone thickness, even when the estimate is approximate, can simply be used in formula (1). However, in the case of operator entry, or onscreen pre-validation of temporal bone thickness, the three-category approach relieves the operator from feeling that an approximate value was less than robust or adequate. Thus, for example, the qualitative temporal bone window factor entered in step S220 may be expressed as one of three values with respect to brain features: difficult recognition, medium recognition, and easy recognition. These choices correspond respectively to high ultrasound pressure, medium ultrasound pressure, and low ultrasound pressure. Also, instead of being limited to three choices of pressure, a table can be used which quantizes adjusted pressure according to increments of treatment depth 134 and temporal bone thickness 142 (step S252). The output pressure/power can be modulated based on the low/mid/high approach, or at a finer gradation level as provided by, for example, a CT readout of the temporal bone thickness 142 of the patient 126 (e.g., a different power level for each additional 0.5 mm or 1.0 mm of temporal bone thickness 142). For example, at a given treatment depth 134, three different adjusted pressures 156 can be user selectable. The three adjusted pressures may be, for instance, 1 MPa for a bone thickness in the range 0.07 cm to 0.15 cm; 1.5 MPa for a bone thickness in the next range up to 0.3 cm; and 2 MPa for a bone thickness that is greater. At a greater treatment depth 134, the pressures shift upward accordingly. Conversely, at a lesser treatment depth 134, the pressures shift downward accordingly. The user interface may ask for entry of the treatment depth, as "Deep", "Average", or "Shallow"; and entry of the temporal bone thickness, as "Thin", "Average", or "Thick." Based on these selections, the controller 118 selects a pressure setting. In particular, values have been pre-assigned to each possible user selection. For "Deep", "Average", and "Shallow", the values may be 3.55, 5.08, and 6.61 cm. The values for "Thin", "Average", and "Thick" may be 0.07, 0.30, and 0.46 cm. The selected values are substituted into formula (1). The selection therefore results in one of nine possible attenuation values. Based on a desired, or target, in situ local pressure, and on the selected attenuation value, one of nine corresponding pressure settings is selected. Thus, the adjusting, by the controller 118, entails selecting from categories formed by stratifying treatment depth 134 and temporal bone thickness 142. The stratifying of each of the treatment depth 134 and the temporal bone thickness 142, may be into three categories. After the adjusted pressure is determined, processing branches forward to the adjusted pressure application step S251.

Therapy could be delivered in an emergency room setting (i.e. Stroke Unit), or in an ambulance/point-of-care setting for the treatment of acute ischemic stroke. Additional uses for what is proposed herein include novel treatments for cardiac tissue reperfusion, blast-induced traumatic brain injury (bTBI) or mild traumatic brain injury (mTBI). Or use can be made in drug delivery to the brain utilizing ultrasound, with systemically injected drug agents and vascular acoustic resonators (VARs), or other specifically designed nanoparticles, enhancing the transport of drugs across the blood-brain barrier using appropriately targeted and defined ultrasound exposures. The intended scope of what is proposed herein extends to other treatments that would benefit from knowing the temporal bone thickness and treatment depth a priori.

An apparatus for patient-specific adjusting of ultrasound output pressure includes a controller configured for adjusting, based on an estimate of thickness of a temporal bone in a head of a medical treatment recipient, a pressure setting. It may also be based on treatment depth. Ultrasound at the adjusted pressure setting is applied. A user interface may be provided for user entry of the estimate, the user interface being further configured for user indication of the treatment depth. Both the entered estimate and the indicated treatment depth may be used in calculating ultrasound attenuation. The user indication can be interactive by virtue of designating, on a display, a location of a treatment target. The calculated attenuation at 1 MHz may be a value, in decibels, that would be estimated by: $(2.70 \times 0.1 + 16.60 \times T + 0.87 \times (D-T-0.1) + 3.02)$, where T is the estimate in centimeters and D is the treatment depth in centimeters.

While the invention has been illustrated and described in detail in the drawings and foregoing description, such illustration and description are to be considered illustrative or exemplary and not restrictive; the invention is not limited to the disclosed embodiments.

For example, every few minutes (e.g., every 10 minutes), or at desired intervals, the STL treatment may be temporarily paused, and the algorithm in FIG. 2 re-executed, to compensate for headset motion or transducer placement, for example.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The word "exemplary" is used herein to mean "serving as an example, instance or illustration." Any embodiment described as "exemplary" is not necessarily to be construed as preferred or advantageous over other embodiments and/or to exclude the incorporation of features from other embodiments. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache and RAM.

A single processor or other unit may fulfill the functions of several items recited in the claims. The mere fact that certain measures are recited in mutually different dependent claims does not indicate that a combination of these measures cannot be used to advantage.

What is claimed is:

1. A method for patient-specific adjusting of ultrasound output power comprising:
   based on an imaging result of applying a medical imaging device to a head of medical treatment recipient, estimating a thickness of a temporal bone in said head, wherein the estimating is based, at least in part on a first user indication of one of a first plurality of categories formed by stratifying the thickness of the temporal bone;
   receiving a treatment depth based on a second user indication of one of a second plurality of categories formed by stratifying the treatment depth;
   calculating an ultrasound attenuation based on the first user indication and the second user indication; and
   adjusting, based on the calculated ultrasound attenuation, a pressure setting of an ultrasound-emitting device, wherein the pressure setting is adjusted to one of a plurality of predefined pressure settings which are based on the first plurality of categories and the second plurality of categories.

2. An apparatus for patient-specific adjusting of ultrasound output pressure, said apparatus comprising:
   a user interface configured for receiving a first user indication of a treatment depth, wherein the first user indication is one of a first plurality of categories formed by stratifying the treatment depth and for receiving a second user indication of an estimate of thickness of a temporal bone in a head of a medical treatment recipient, wherein the second user indication is one of a second plurality of categories formed by stratifying the thickness of the temporal bone;
   a controller configured for calculating, based on the indicated treatment depth and the estimate of thickness of the temporal bone in the head of the medical treatment recipient, an ultrasound attenuation and for adjusting a pressure setting based on the calculated ultrasound attenuation, wherein the pressure setting is adjusted to one of a plurality of predefined pressure settings which are based on the first plurality of categories and the second plurality of categories; and
   an ultrasound-emitting device for applying ultrasound at the adjusted pressure setting.

3. The apparatus of claim 2, further comprising a display, wherein said first user indication is interactive by virtue of designating, on said display, a location of a treatment target.

4. The apparatus of claim 2, wherein the calculated ultrasound attenuation is a value, in decibels, that is in a range from $0.9 \times (2.70 \times 0.1 + 16.60 \times T + 0.87 \times (D-T-0.1) + 3.02)$ to $1.1 \times (2.70 \times 0.1 + 16.60 \times T + 0.87 \times (D-T-0.1) + 3.02)$, where T is said estimate of thickness in centimeters and D is said treatment depth in centimeters.

5. The apparatus of claim 2, wherein the first plurality of categories comprises three categories and the second plurality of categories comprises three categories.

6. The apparatus of claim 2, wherein said applying ultrasound is performed with a central frequency in a range from 0.8 to 1.2 megahertz.

7. The apparatus of claim 2, comprising an ultrasound imaging device configured for acquiring an ultrasound image.

8. The apparatus of claim 2, said controller being configured for causing said user interface to issue a user prompt for at least one of the first user indication or the second user indication.

9. The apparatus of claim 2, wherein said applying ultrasound is performed with a central frequency in a range from 0.9 to 1.1 megahertz.

10. The apparatus of claim 2, wherein a number of the plurality of predefined pressure settings is equal to nine.

11. A non-transitory computer readable medium embodying a program for patient-specific adjusting of ultrasound output pressure, said program having instructions executable by a processor for performing a plurality of acts, among said plurality there being the acts of:
receiving a first user indication of a treatment depth, wherein the first user indication is one of a first plurality of categories formed by stratifying the treatment depth;
receiving a second user indication of an estimate of thickness of a temporal bone in a head of a medical treatment recipient, wherein the estimate is one of a second plurality of categories formed by stratifying the thickness of the temporal bone;
calculating an ultrasound attenuation based at least in part on the treatment depth and the estimate of thickness;
adjusting, based on the calculated ultrasound attenuation, a pressure setting of an ultrasound-emitting device, wherein the pressure setting is adjusted to one of a plurality of predefined pressure settings which are based on the first plurality of categories and the second plurality of categories; and
controlling the ultrasound-emitting device to apply ultrasound at the adjusted pressure setting.

12. The non-transitory computer readable medium of claim 11, wherein among said plurality of acts, there further being the act of controlling the ultrasound-emitting device to emit, at the adjusted pressure setting, the ultrasound at a frequency in the range from 0.8 to 1.2 megahertz.

13. The non-transitory computer readable medium of claim 12, said frequency being in the range from 0.9 to 1.1 megahertz.

* * * * *